US 6,677,151 B2

(12) United States Patent
Sandell

(10) Patent No.: US 6,677,151 B2
(45) Date of Patent: Jan. 13, 2004

(54) DEVICE AND METHOD FOR THERMAL CYCLING

(75) Inventor: Donald R. Sandell, San Jose, CA (US)

(73) Assignee: Applera Corporation, Foster City, CA (US)

(*) Notice: Subject to any disclaimer, the term of this patent is extended or adjusted under 35 U.S.C. 154(b) by 186 days.

(21) Appl. No.: 10/058,927

(22) Filed: Jan. 30, 2002

(65) Prior Publication Data

US 2003/0143723 A1 Jul. 31, 2003

(51) Int. Cl.[7] .............................. C12M 1/38; C12Q 1/68
(52) U.S. Cl. ........................... 435/287.2; 435/287.3; 435/288.7; 435/303.1; 435/6; 435/91.2; 422/65
(58) Field of Search .................... 435/6, 91.2, 286.1, 435/286.2, 287.2, 287.3, 288.4, 288.7, 303.1, 305.3, 808, 810; 422/63–65, 82.05, 82.08, 82.11, 99, 102, 104; 436/47, 164, 165, 809; 219/428; 250/328; 356/440

(56) References Cited

U.S. PATENT DOCUMENTS

| | | |
|---|---|---|
| 4,097,116 A | 6/1978 | Kuroha |
| 4,313,679 A | 2/1982 | Wolff et al. |
| 4,577,141 A | 3/1986 | Saiki et al. |
| 4,865,461 A | 9/1989 | Taylor et al. |
| 5,416,329 A | 5/1995 | Sonne et al. |
| 5,489,532 A | 2/1996 | Charm et al. |
| 5,616,301 A | 4/1997 | Moser et al. |
| 5,720,923 A | 2/1998 | Haff et al. |
| 5,736,106 A | 4/1998 | Ishiguro et al. |
| 5,795,547 A | 8/1998 | Moser et al. |
| 5,897,842 A | 4/1999 | Dunn et al. |
| 5,928,907 A | 7/1999 | Woudenberg et al. |
| 6,015,674 A | 1/2000 | Woudenberg et al. |
| 6,033,880 A | 3/2000 | Haff et al. |
| 6,036,920 A * | 3/2000 | Pantoliano et al. ........... 422/67 |
| 6,043,880 A | 3/2000 | Andrews et al. |
| 6,132,996 A | 10/2000 | Hunicke-Smith |
| 6,197,572 B1 | 3/2001 | Schneebeli |
| 6,210,958 B1 | 4/2001 | Brust et al. |
| 6,448,066 B1 | 9/2002 | Wheatcroft |

FOREIGN PATENT DOCUMENTS

| | | |
|---|---|---|
| EP | 0 311 440 A2 | 4/1989 |
| WO | WO 97/36681 | 10/1997 |
| WO | WO 00/25922 | 5/2000 |
| WO | WO 01/28684 A2 | 4/2001 |

OTHER PUBLICATIONS

International Search Report dated Apr. 21, 2003 issued in PCT/US03/01061.
Co–pending application No. 09/897,500, Inventors: Bordenkircher et al., filed Jul. 3, 2001, Title: PCR sample handling device.
Co–pending application No. 09/977,225, Inventors: Freudenthal et al., filed Oct. 16, 2001, Title: System for filling substrate chambers with liquid.

* cited by examiner

Primary Examiner—William H. Beisner

(57) ABSTRACT

A thermal cycling device for performing nucleic acid amplification on a plurality of biological samples positioned in a sample well tray. The thermal cycling device includes a sample block assembly, an optical detection system, and a sample well tray holder configured to hold the sample well tray. The sample block assembly is adapted for movement between a first position permitting the translation of the sample well tray into alignment with sample block assembly, and a second position, upward relative to the first position, where the sample block assembly contacts the sample well tray. A method of performing nucleic acid amplification on a plurality of biological samples positioned in a sample well tray in a thermal cycling device is also provided.

35 Claims, 8 Drawing Sheets

DEVICE AND METHOD FOR THERMAL CYCLING

FIELD OF THE INVENTION

The present invention relates generally to a thermal cycling device and method of performing nucleic acid amplification on a plurality of biological samples positioned in a sample well tray. More particularly, the present invention relates in one aspect to a thermal cycling device and method of real-time detection of a nucleic acid amplification process such as polymerase chain reaction (PCR).

BACKGROUND

Biological testing has become an important tool in detecting and monitoring diseases. In the biological testing field, thermal cycling is used to amplify nucleic acids by, for example, performing PCR and other reactions. PCR in particular has become a valuable research tool with applications such as cloning, analysis of genetic expression, DNA sequencing, and drug discovery.

Recent developments in the field have spurred growth in the number of tests that are performed. One method for increasing the throughput of such biological testing is to provide real-time detection capability during thermal cycling. Real-time detection increases the efficiency of the biological testing because the characteristics of the samples can be detected while the sample well tray remains positioned in the thermal cycling device, therefore not requiring removal of the sample well tray to a separate area prior to testing of the samples. In typical real-time thermal cycling devices, the sample well tray is removed after detection is completed.

SUMMARY OF THE INVENTION

Various aspects of the invention generally relate to a thermal cycling device in which the sample block assembly may be vertically moved so that the sample well tray may be inserted and removed from the thermal cycling device. The thermal cycling device can be a real-time device. During such movement of the sample block assembly and sample well tray, the optical detection system can remain substantially stationary.

According to one aspect, the invention comprises a thermal cycling device. The thermal cycling device includes a sample block assembly, an optical detection system, and a sample well tray holder. The sample well tray holder includes a tray-receiving region configured to hold a sample well tray. The optical detection system is positioned above the sample block assembly. The sample well tray holder is configured to translate the sample well tray into alignment with the sample block assembly. The sample block assembly is adapted for movement between a first position permitting the translation of the sample well tray into alignment with the sample block assembly, and a second position, upward relative to the first position, where the sample block assembly contacts the sample well tray.

In another aspect, the optical detection system is adapted to remain substantially stationary during insertion and removal of the sample well tray from the thermal cycling device. In a further aspect, the thermal cycling device further includes a positioning mechanism configured to translate the sample block between the first and second positions.

In yet another aspect, the invention comprises a method of performing nucleic acid amplification on a plurality of biological samples positioned in a sample well tray in a thermal cycling device. The method includes the step of placing the sample well tray into a sample well tray holder. The method further includes the step of translating the sample well tray holder and sample well tray into the thermal cycling device until the sample well tray is aligned with a sample block assembly positioned beneath the sample well tray. The method further includes the step of translating the sample block assembly from a first position to a second position. In the first position, the sample block assembly permits the sample well tray to translate into alignment with the sample block assembly. In the second position, the sample block assembly is positioned vertically upward relative to the first position to contact the sample well tray.

The method can further comprise the step of thermally cycling the device while simultaneously optically detecting the samples. The method can further comprise translating the sample block assembly from the second position to the first position. Finally, the method can comprise the step of removing the sample well tray holder and sample well tray from the thermal cycling device. In various embodiments, the optical detection system remains substantially stationary throughout the above steps.

In another aspect, the invention comprises a thermal cycling device. The thermal cycling device includes an optical detection system, a sample block, and a sample well tray holder. The sample block is adapted for movement along a first path, toward and away from the optical detection system. The sample well tray holder includes a tray-receiving region. The sample well tray holder is adapted for movement along a second path, toward and away from a position whereat the tray-receiving region is disposed between the optical detection system and the sample block. The optical detection system can be adapted to remain substantially stationary during movement of the sample block and the sample well tray holder along the first and second paths.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention. In the drawings.

DESCRIPTION OF CERTAIN EMBODIMENTS

Figure 1:
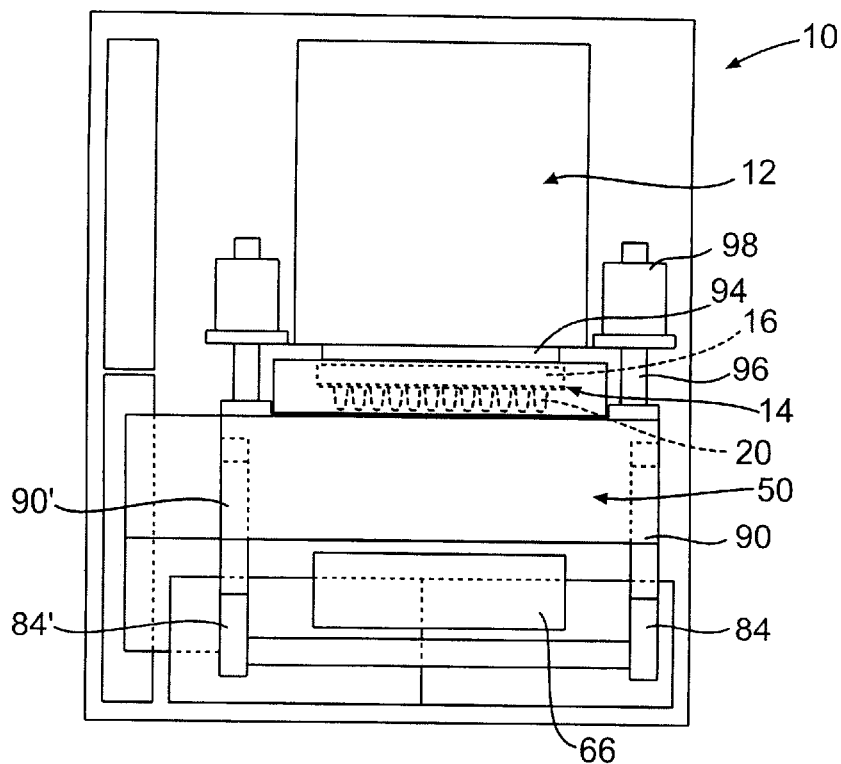
FIG. 1 is a front view of an exemplary embodiment of a thermal cycling device according to the present invention.

Reference will now be made to certain exemplary embodiments of the invention, examples of which are illustrated in the accompanying drawings. Wherever possible, the same reference numbers are used in the drawings and the description to the same or like parts.

In accordance with certain embodiments, a thermal cycling device is provided. In one aspect, the thermal cycling device may perform nucleic acid amplification on a plurality of biological samples positioned in a sample well tray. In certain embodiments, the thermal cycling device includes a sample block assembly, an optical detection system positioned above the sample block assembly, and a sample well tray holder with a tray-receiving region configured to hold the sample well tray. In certain aspects, the sample block assembly is adapted for movement between a first position permitting the translation of the sample well tray into alignment with the sample block assembly, and a second position, upward relative to the first position, where the sample block assembly contacts the sample well tray. The thermal cycling device may also include a positioning mechanism for translating the sample block between the first and second positions.

Although the terms "horizontal," "vertical," "upward," and "downward" are used in describing various aspects of the present invention, it should be understood that such terms are for purposes more easily describing the invention, and do not limit the scope of the invention.

In various embodiments, such as illustrated in FIGS. 1, 2A–2C, and 5–6, the thermal cycling device 10 for performing nucleic acid amplification on a plurality of biological samples includes one or more of: a sample block assembly 50; an optical detection system 12 for detecting the characteristics of the samples positioned in a sample well tray 14; a sample well tray holder 30; and a positioning mechanism 70 connected to the sample block assembly, the positioning mechanism being configured to impart vertical movement on the sample block assembly.

The thermal cycling device is typically configured to perform nucleic acid amplification. One common method of performing nucleic acid amplification of biological samples is polymerase chain reaction (PCR). Various PCR methods are known in the art, as described in, for example, U.S. Pat. Nos. 5,928,907 and 6,015,674 to Woudenberg et al., the complete disclosures of which are hereby incorporated by reference for any purpose. Other methods of nucleic acid amplification include, for example, ligase chain reaction, oligonucleotide litigations assay, and hybridization assay. These and other methods are described in greater detail in U.S. Pat. Nos. 5,928,907 and 6,015,674.

In one embodiment, the thermal cycling device performs real-time detection of the nucleic acid amplification of the samples during thermal cycling. Real-time detection systems are known in the art, as also described in greater detail in, for example, U.S. Pat. Nos. 5,928,907 and 6,015,674 to Woudenberg et al., incorporated herein above. During real-time detection, various characteristics of the samples are detected during the thermal cycling in a manner known in the art. Real-time detection permits more accurate and efficient detection and monitoring of the samples during the nucleic acid amplification.

In accordance with various embodiments, the thermal cycling device includes an optical detection system. As embodied herein and shown in FIGS. 1 and 2A–2C, an optical detection system 12 is positioned above the sample block assembly 50. The optical detection system 12 is configured to detect and monitor the characteristics of the samples in the sample well tray 14 in real-time during the thermal cycling. Suitable structures and methods for the optical detection system 12 are well known in the art. The optical detection system may use any known structure or method. In one example, the optical detection system would include a quartz bulb with a CCD camera, in a manner known in the art. In another example, the optical detection system may include a fluorescence based system with a lens and a fiber optics for each cable as described in U.S. Pat. Nos. 5,928,907 and 6,015,674 to Woudenberg et al, incorporated herein above. Alternatively, the optical detection system may include any known system using a single light source for each sample well, in a manner known in the art. Likewise, the optical detection system may include any other type suitable for use with the thermal cycling device of the present invention.

In various embodiments, optical detection system 12 is substantially stationarily mounted in the thermal cycling device. The optical detection system can be configured so that the optical detection system remains substantially stationary during insertion of a sample well tray holder and sample well tray into the thermal cycling device, during thermal cycling of the sample well tray, during removal of the sample well tray holder and sample well tray from the thermal cycling device, and at all stages in between the above steps. By remaining substantially stationary, the optical system reduces the potential for misalignment of the optical components. For purposes of this invention, the term "substantially stationary" does not mean that the optical detection system is completely stationary, rather, the term includes any vibrations or movements caused by normal operation of the thermal cycling device.

The thermal cycling device may be configured for use with any type of sample well tray, including, for example, 96-well sample well trays, 384-well sample trays, and microcard sample trays. The size and shape of these sample well trays are well known in the art. Examples of 96-well sample well trays suitable for use in the present invention are described in WO 00/25922 to Moring et al., the complete disclosure of which is hereby incorporated by reference for any purpose. Examples of sample well trays of the microcard type suitable for use in the present invention are described in WO 01/28684 to Frye et al., the complete disclosure of which is hereby incorporated by reference for any purpose, WO97/36681 to Woudenberg et al., the complete disclosure of which is hereby incorporated by reference for any purpose, U.S. application Ser. No. 09/897,500, filed Jul. 3, 2001, assigned to the assignee of the present invention, the complete disclosure of which is hereby incorporated by reference for any purpose, and U.S. application Ser. No. 09/977,225, filed Oct. 16, 2001, assigned to the assignee of the present application, the complete disclosure of which is hereby incorporated by reference for any purpose. Sample well trays having any number of sample wells and sample well sizes may also be used with the thermal cycling device of the present invention. In the example shown in the figures, the volume of the sample wells may vary anywhere from about 0.01 $\mu$l to thousands of microliters ($\mu$l), with a volume between 10 to 500 $\mu$l being typical.

As embodied herein and shown in FIGS. 1, 2A–2C, and 5, the sample well tray 14 can include a rectangular top portion 16 having a top surface 18 and bottom surface 24. The top surface 18 defines openings for a plurality of sample wells 20 of any known size and shape. In the example shown in FIGS. 1–6, the sample well tray includes ninety-six sample wells positioned in a well-known 8×12 array. In the embodiment shown, the top portion 16 of the sample well tray is rectangular. In the embodiment shown in the figures, the sample wells are conical shape recesses extending downwardly from the top surface 18 in a known manner. Each sample well includes a sample well bottom surface 22 for engaging with corresponding recesses in the sample block assembly 50. It is well understood that any type of sample well configuration may be used with the present invention, including for example, a 384-well sample well tray and a microcard type sample tray.

In accordance with various embodiments, the thermal cycling device can include a sample well tray holder having a tray-receiving region configured to hold the sample well tray. The sample well tray holder can be configured to translate the sample well tray into alignment with a sample block assembly. As described herein and shown in FIGS. 1, 2A–2C, and 5, the sample well tray holder is generally designated by reference number 30. The sample well tray holder is configured so that the sample well tray may be supported thereon, particularly during insertion of the sample well tray into the thermal cycling device, and during removal of the sample well tray from the thermal cycling device. In various embodiments, the sample well tray holder 30 is generally rectangular in shape.

Figure 5:
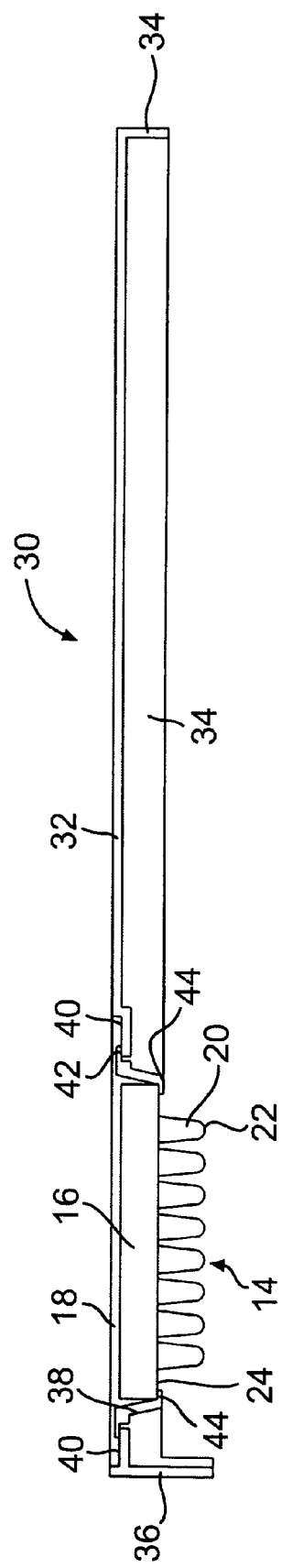
FIG. 5 is a side cross sectional view of a sample well tray holder, used with the present invention, with a sample well tray positioned thereon.

With particular reference to FIG. 5, the sample well tray holder 30 includes a top surface 32 and a side surface 34 that extends around the periphery of the sample well tray holder. The side surface in the front of the device is designated by reference number 36. The sample well tray holder further includes a tray-receiving region configured to hold a sample well tray. In the embodiment shown in FIG. 5, the tray-receiving region is defined by a downwardly projecting holder structure 38 in the top surface 32. The downwardly projecting holder structure 38 is positioned on a first recessed portion 40 of the top surface 32. The downwardly projecting holder structure 38 includes a horizontally projecting annular projection 42 for engaging the top surface of the first recessed portion 40 of the top surface 32. The downwardly projecting holder structure 38 further comprises a projection 44 that slopes inwardly. The inside of the projection 44 defines a rectangular opening or recess slightly smaller than the sample well tray 16. The rectangular opening or recess is dimensioned to receive a sample well tray. In particular, the projection 44 is dimensioned so that the bottom surface 24 of the sample well tray may rest on the top surface of the projection 44, as shown in FIG. 5. The projecting holder structure may be shaped to be angled inwardly in order to ease the removal of the sample well tray from the sample well tray holder.

The sample well tray holder 30 and sample well tray 14 are dimensioned so that they are capable of passing between the optical detection system 12 and the sample block assembly 50 without interference during insertion into and removal from the thermal cycling device. The sample well tray is configured so that it can horizontally translate into and out of the thermal cycling device on the sample well tray holder. In order to facilitate insertion or removal of the sample well tray holder, bearing surfaces (not shown) may be provided on the sample well tray holder and/or thermal cycling device. The sample well tray holder may be horizontally translated either manually or automatically.

Figure 6:
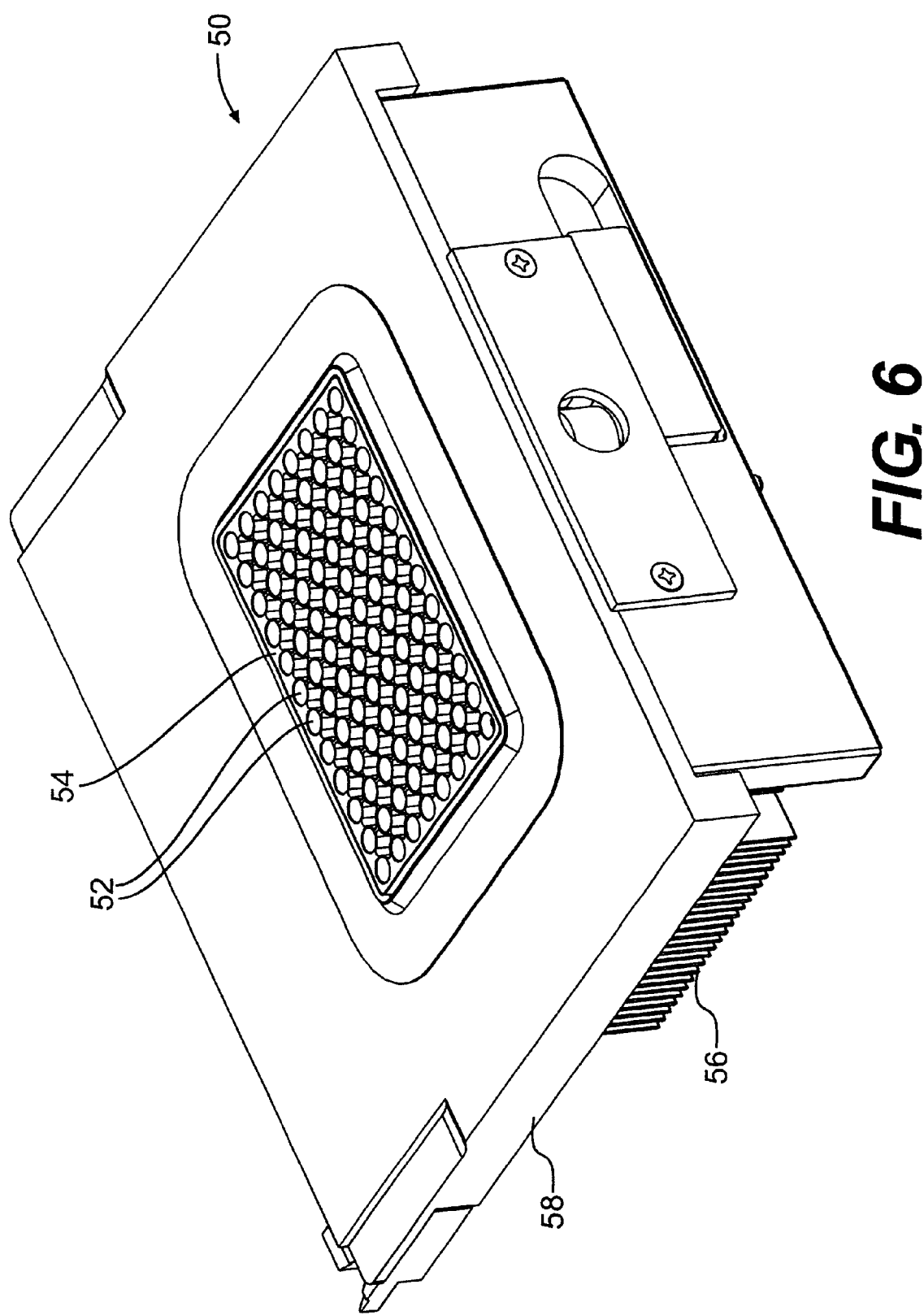
FIG. 6 is a perspective view of one embodiment of a sample block assembly used in the device of the invention.

In accordance with various embodiments, the thermal cycling device can include a sample block assembly configured to receive the sample well tray thereon. As described herein and shown in FIGS. 1, 2A–2C, 5, and 6, a sample block assembly is generally designated by reference number 50. It is to be understood that the sample block assembly shown in FIG. 6 is by way of example only, and the invention is not limited to the sample block assembly shown in FIG. 6. The sample block assembly shown in FIG. 6 includes a sample block 58 and a heat sink 56. Sample blocks are well known in the art. Sample blocks may be made of any suitable material, such as aluminum. The sample block assembly typically includes at least one heating element. In one embodiment, the at least one heating element includes a peltier heater. Methods of heating and cooling a sample block during and after thermal cycling are known in the art. The sample block 58 shown in FIG. 6 includes a top surface 54 with a plurality of recess 52 on the top surface. The recesses are arranged to correspond to the sample wells of the sample well tray. For example, in the embodiment shown in FIG. 6, the sample block assembly includes ninety-six recesses for engaging with a 96-well sample well tray. Alternatively, the sample block assembly can have any number of recesses. For example, the number of recesses can equal the number of sample wells. In an embodiment with a 384-well sample tray, the sample block assembly would typically have at least 384 recesses. In an embodiment using a microcard type sample tray, the sample block need not have recesses.

Heat sink 56 may be any known type of heat sink. Additionally, a convection unit such as a fan may be positioned adjacent the sample block assembly. In the embodiment shown in FIGS. 1, 2A–2C, and 5–6, the convection unit comprises a fan 66 positioned below the sample block assembly 50. In one embodiment, the fan 66 creates a flow of cooling air against the heat sink 56 in order to cool the sample block. Alternatively, the fan may be used with a heater in order to create a flow of hot air against the heat sink in order to heat the sample block. In certain embodiments, the fan is mounted so that it moves vertically with the sample block assembly. In other embodiments, the fan may be stationarily mounted in the thermal cycling device.

In accordance with various embodiments, the thermal cycling device can include a positioning mechanism connected to the sample block assembly, the positioning mechanism being configured to vertically translate the sample block assembly between a first or "downward" position and a second or "upward" position. The positioning mechanism can be configured to translate the sample block assembly between the first position, where the sample block assembly permits the translation of the sample well tray into alignment with the sample block assembly, and the second position, upward relative to the first position, where the sample block assembly contacts the sample well tray.

Figure 2A:
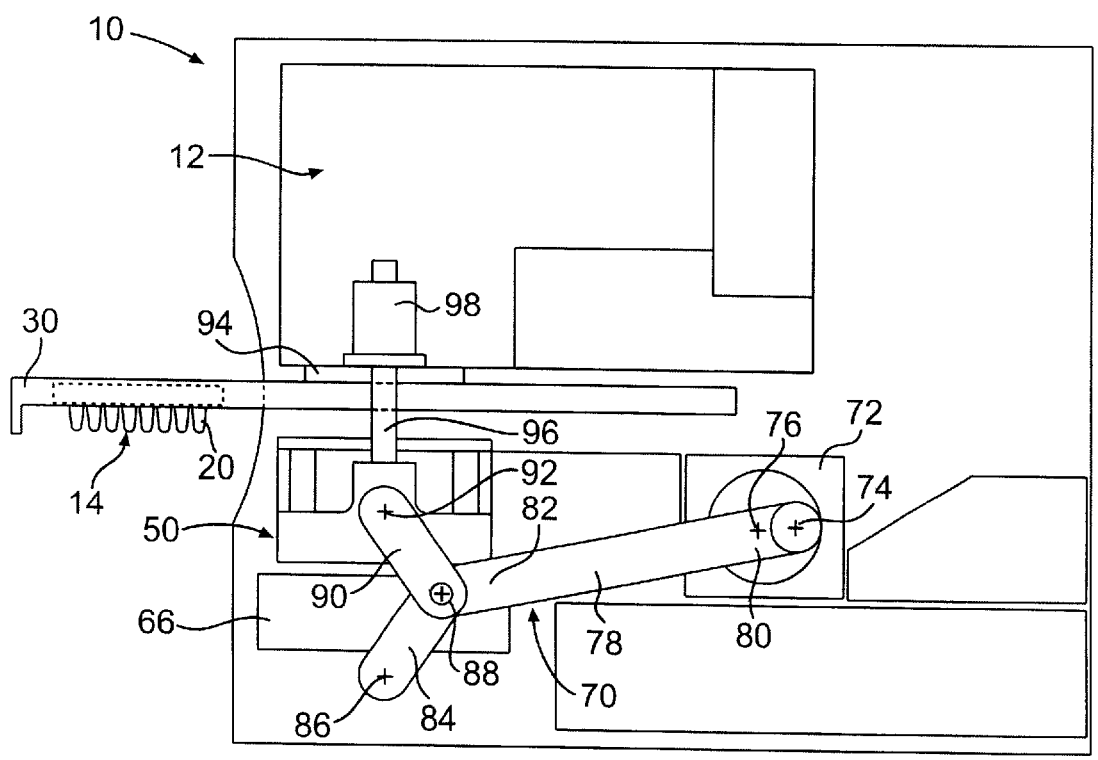
FIG. 2A is side view of an embodiment of the device of FIG. 1, with a sample well tray positioned outside of the device.
Figure 2B:
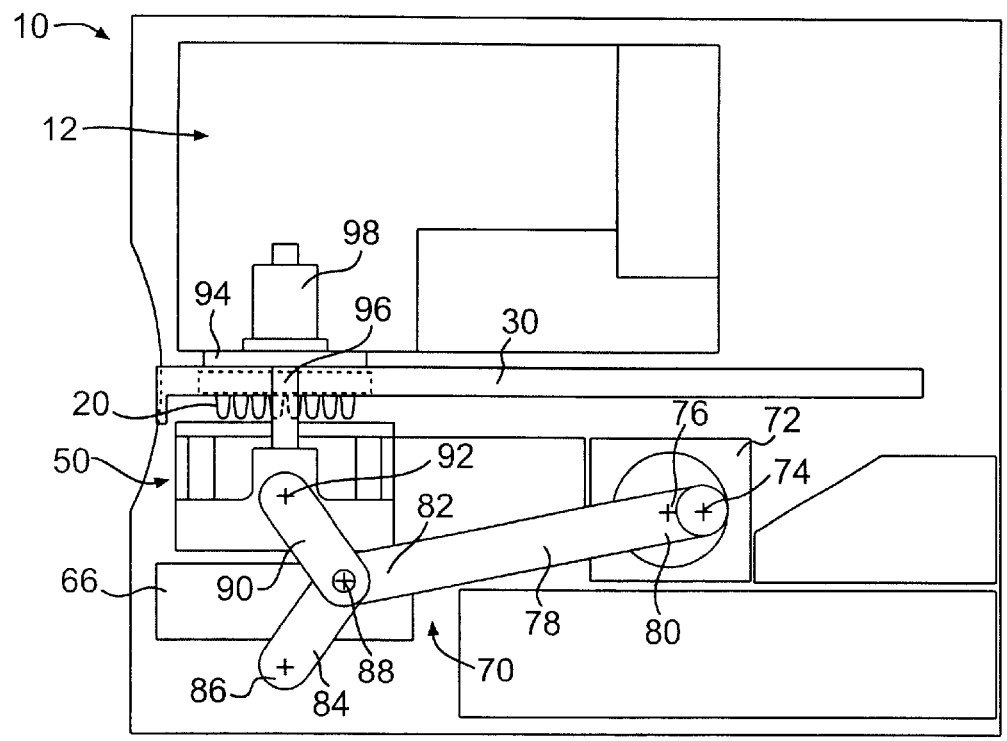
FIG. 2B is a side view of the device of FIG. 1, with the sample well tray inserted into the device.

An embodiment of the positioning mechanism is illustrated in FIGS. 1 and 2A–2C. In the embodiment shown in FIGS. 1 and 2A–2C, the positioning mechanism is generally designated by reference number 70. The positioning mechanism is connected to the sample block assembly 50. The positioning mechanism allows insertion and removal of the sample well tray by moving the sample block assembly in the vertical direction. FIGS. 2A and 2B show the downward or "first" position of the sample block assembly. In the downward position, a gap is created between the top of the sample block assembly 50 and a bottom portion 94 of the optical detection system of sufficient size so that the sample well tray holder and sample well tray may be inserted therebetween. In the first position, the sample block is "away" from the optical detection system.

Figure 2C:
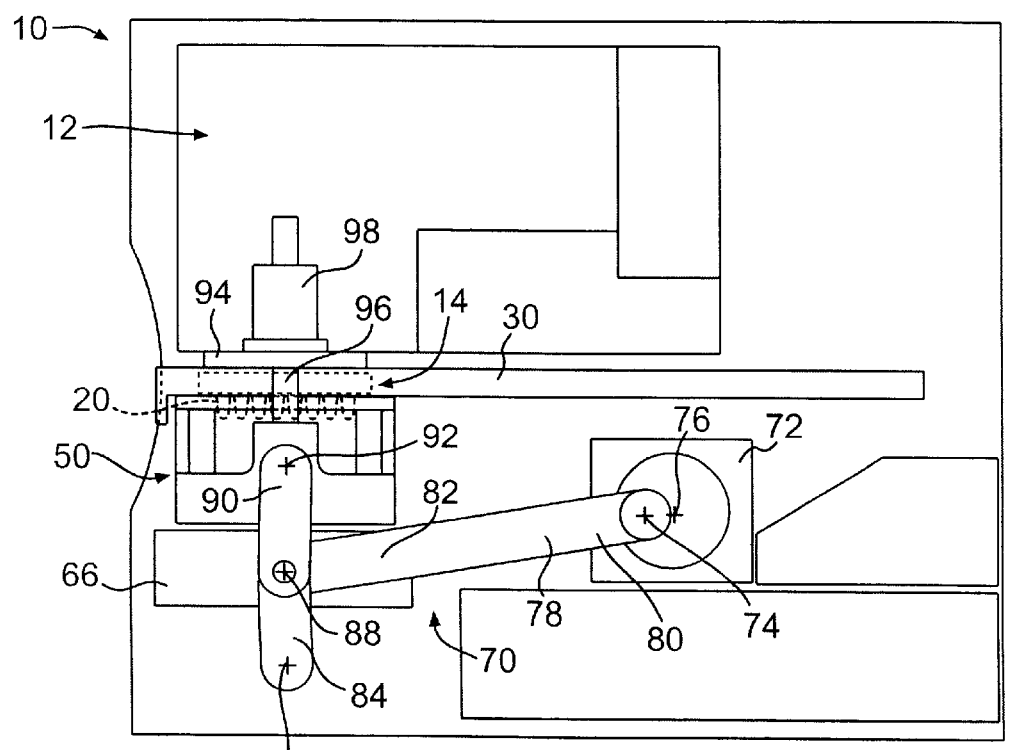
FIG. 2C is a side view of the device of FIG. 1, with the sample well tray inserted into the device and a sample block assembly in an upward position for engaging the sample well tray.

In a second or "upward" position shown in FIG. 2C, the sample block assembly 50 is vertically upward relative to the downward or "first" position. In the upward position, the top surface 54 of the sample block 58 presses against the bottom of the sample well tray 14 so that the recesses 52 mate with the sample well bottom surfaces 22. In various embodiments using a microcard, a top surface of the sample block can press against a bottom surface of the microcard. In the second position, the sample block is "toward" the optical detection system. The sample block assembly is adapted for movement toward and away from the optical detection system along a predetermined vertical path.

In the embodiment shown in FIGS. 1 and 2A–2C, the positioning mechanism 70 includes a plurality of links. The arrangement of links shown in FIGS. 1 and 2A–2C is by way of example only. The plurality of links includes a first link 78 as shown in FIGS. 2A–2C. The first link 78 is shown as being in the shape of a connecting rod, however, the first link may have any number of different shapes. First link 78 includes a first end 80 rotatably connected to a motor 72 at a pivot point 74. Motor 72 can be any known type of motor that is capable of imparting a translational or rotational force on the first link 78. As shown in FIGS. 2A–2C, the motor causes pivot point 74 of the first end 80 to revolve around a central axis 76 of the motor. The revolution of the first end 80 about the central axis of the motor causes the first link to translate.

As shown in FIGS. 2A–2C, a second end 82 of the first link is rotatably connected to a first end of a second link 84 at pivot point 88. The second link has a second end rotatably connected to stationary pivot point 86. The second link 84 pivots about stationary pivot point 86 when the motor causes movement of the first link 78.

The second end 82 of the first link is rotatably connected to a first end of a third link 90 at pivot point 88. The second end of the third link 90 is rotatably connected to the sample block assembly at pivot point 92. By revolution of the first end of the first link about the central axis 76 of the motor, the first link causes the first end of the second link 84 to rotate partially about the stationary pivot point 86, thus causing the third link to press upward against the sample block assembly at pivot point 92. The positioning mechanism is connected to the sample block assembly by, for example, a pin at pivot point 92. As a result of this linkage arrangement, the positioning mechanism causes the sample block assembly to move vertically from the downward or "first" position shown in FIGS. 2A and 2B to the upward or "second" position shown in FIG. 2C. It should be understood that the positioning mechanism of FIGS. 2A–2C is by way of example only.

As shown in FIG. 1, the positioning mechanism 70 may include two sets of links, one on each lateral side of the sample block assembly. The second set of links is a mirror image of the first set of links. In FIG. 1, the second set of links includes first link (not shown), second link 84', and third link 90'. With a configuration having two sets of links, an individual motor may be utilized for each of the sets of links, or alternatively, a single motor may be utilized for both sets of links. In another variation, a single set of links may be used instead of two sets of links. In a further variation, more than two sets of links may be used.

The positioning mechanism may also include at least one guide member for guiding the sample block assembly in the vertical direction. The guide member can be configured to prevent the sample block assembly from moving in the horizontal direction. Any known type of guide member may be utilized. In the embodiment shown in FIGS. 1 and 2A–2C, the guide member includes a plurality of vertical shafts 96 fixedly attached to the lateral sides of the sample block assembly 50. As shown in FIG. 1, the vertical shafts are positioned on each lateral side of the sample well tray holder 30 and sample well tray 14. Each vertical shaft 96 is received within bearing member 98. Bearing member is stationarily mounted adjacent the optical detection system. Each vertical shaft 96 slides within a corresponding cylindrical opening in the bearing member 98. The bearing members 98 and vertical shafts 96 may include any type of known bearing arrangement.

Alternatively, in another variation, the vertical shaft could be stationarily fixed to the thermal cycling device so that the sample block assembly translates vertically relative to the vertical shaft. With such an arrangement, the bearing structures would be mounted within cylindrical openings in the sample block assembly for receiving the vertical shafts.

The guide member may be any other type of known guide member capable of limiting movement of the sample block assembly in the horizontal direction as the sample block assembly is moved in the vertical direction. For example, the guide member could include any type of vertical guiding structure adjacent the sample block assembly. It should be understood that the guide member shown in FIGS. 2A–2C is by way of example only.

An operation of the thermal cycling device for the embodiment of FIGS. 1 and 2A–2C is further described below. First, with the sample well tray holder 30 in an outward position as shown in FIG. 2A, a sample well tray 14 is placed in the sample well tray holder. The sample well tray can be dropped into the recess defined by downwardly projecting holder structure 38 shown in FIG. 5. The sample well tray 14 may be placed in the sample well tray holder 30 either manually or robotically.

In FIG. 2A, the sample block assembly 50 is in a downward or "first" position so that a gap is created between the optical detection system 12 and the uppermost surface of the sample block 58. The gap that is created is larger than the vertical dimension of the sample well tray holder 30 and sample well tray 14.

After the sample well tray 14 is placed in the sample well tray holder 30, the sample well tray holder is horizontally translated into the thermal cycling device 10 until the sample well tray reaches a position where the sample wells of the sample well tray align with the recesses 52 of the sample block 58. The horizontal translation may be caused by an operator or a robot pressing on the sample well tray. In the embodiment shown in FIGS. 1 and 2A–2C, the sample well tray holder 30 can be horizontally translated until each of the ninety-six sample wells align with a corresponding recess 52 in the sample block 58. FIG. 2B shows the sample well tray holder 30 and sample well tray 14 in the position where the sample wells 20 are aligned with corresponding recesses in the sample block 58. As shown in FIG. 2B, the sample block assembly 50 can remain in the downward position until the sample well tray is fully inserted into the thermal cycling device and aligned.

After the sample well tray 14 has been fully inserted into the thermal cycling device 10 and proper alignment has been achieved between the sample wells 20 and the recesses 52 of the sample block (as shown in FIG. 2B), the motor 72 can be actuated to begin a revolution of the first end 80 of the first link 78. As the first end 80 of the first link 78 begins to revolve around the central axis 76 of the motor, the pivot point 88 is moved leftward as shown in FIG. 2C, and the pivot point 92 of the second end of the third link imparts an upward force on the sample block assembly 50. As a result, the sample block assembly 50 is moved upward so that the top surface 54 of the sample block firmly contacts the bottom surface of the sample well tray 14. In the upward position (also referred to as the "second position") shown in FIG. 2C, the sample block assembly 50 is firmly positioned against the sample well tray 14 so that the sample wells 22 are seated against the sample block. The thermal cycling device 10 is now ready for thermal cycling processes.

At any desired time, e.g., after the thermal cycling processes are completed, the sample well tray 14 can be removed by actuating the motor so that the sample block assembly 50 moves to a downward position (as shown in FIG. 2B), and then horizontally translating the sample well tray holder 30 and sample well tray 14 to the position shown in FIG. 2A. The sample well tray 14 may then be removed from the sample well tray holder 30.

The amount of vertical displacement of the sample block assembly 50 between the downward ("first") and upward ("second") positions depends on the specific application, the type and size of sample well tray that is utilized, and other practical concerns. For example, in an application for use with a 96-well sample well tray, the amount of vertical displacement would typically be between about 0.5 to 1.5 inches, but it could be much greater or much less. In an application with a 384-well sample tray having smaller sample wells, or a microcard, the amount of vertical displacement of the sample block assembly may be less. For practical purposes however, it may also be desirable to vertically displace the sample block assembly a much greater distance in order to provide better access to the inside of the device for inspection or maintenance.

In accordance with various embodiments, the optical detection system 12 can be mounted in a substantially stationary manner in the thermal cycling device during insertion and removal of the sample well tray to and from the thermal cycling device, during thermal cycling, and during all steps therebetween.

In accordance with further various embodiments of the positioning mechanism, the plurality of links comprises a first link and a second link. The first link has a first end rotatably connected to a stationary pivot point. The first link also has a second end comprising a handle for manual manipulation of the first link. The second link has a first end rotatably connected to a pivot point on the first link. The second link also has a second end rotatably connected to the sample block assembly.

Figure 3A:
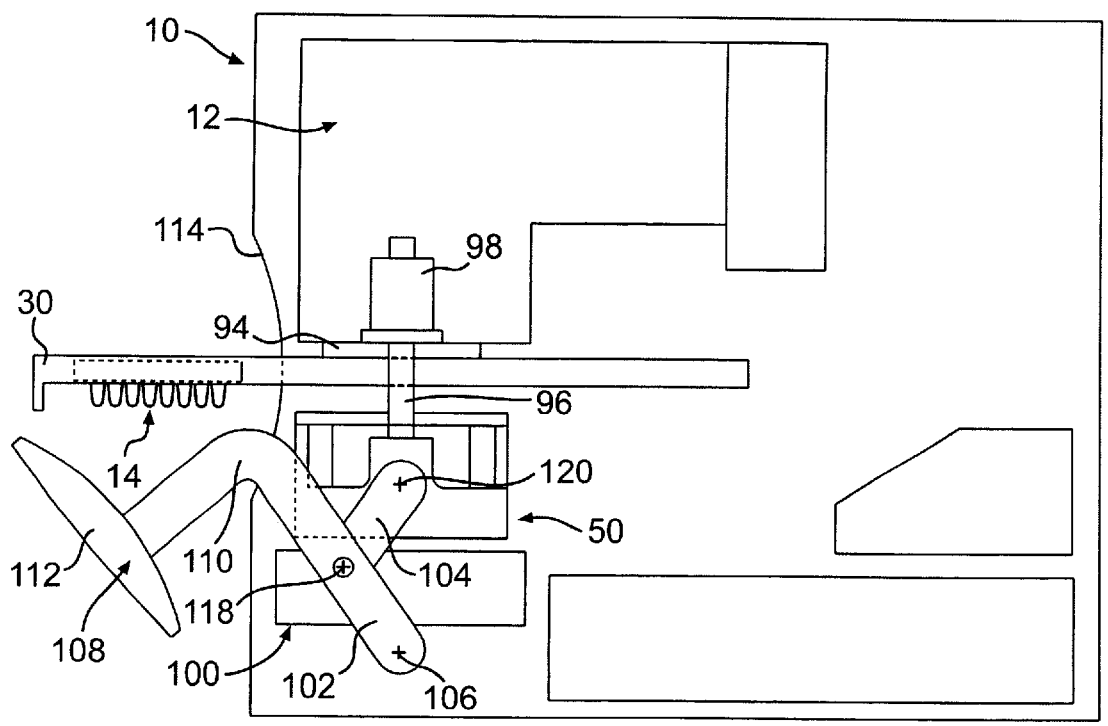
FIG. 3A is a side view of another embodiment of the thermal cycling device of the invention, with a sample well tray positioned outside of the device.
Figure 3B:
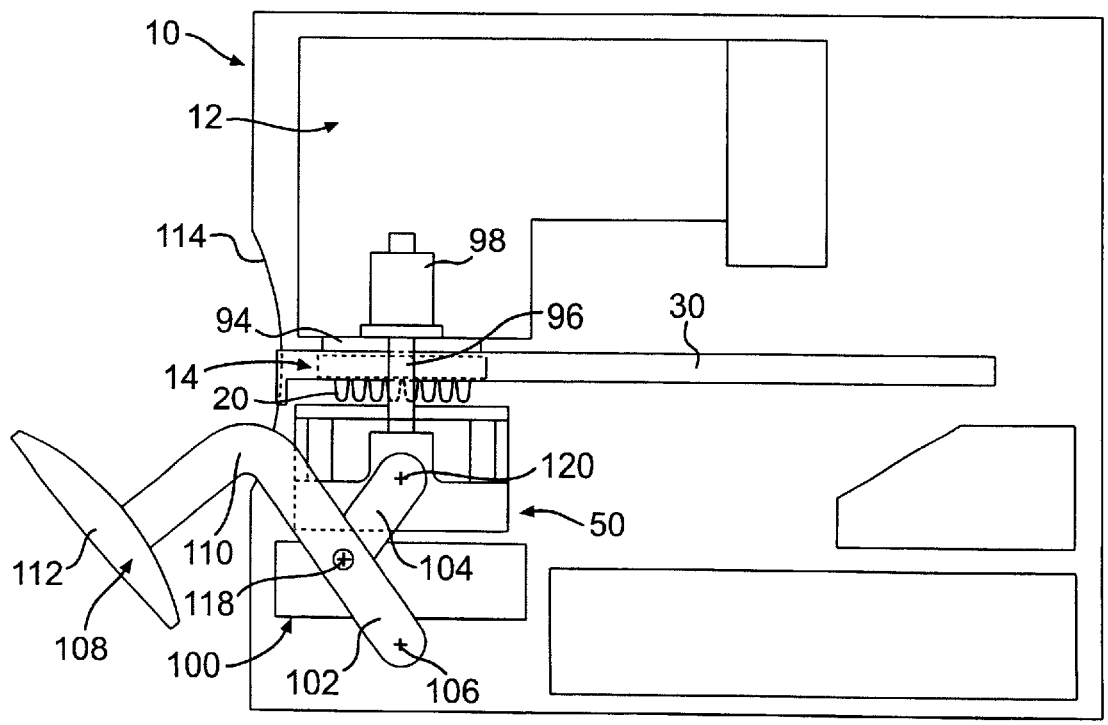
FIG. 3B is a side view of the device of FIG. 3A, with the sample well tray inserted into the device.
Figure 3C:
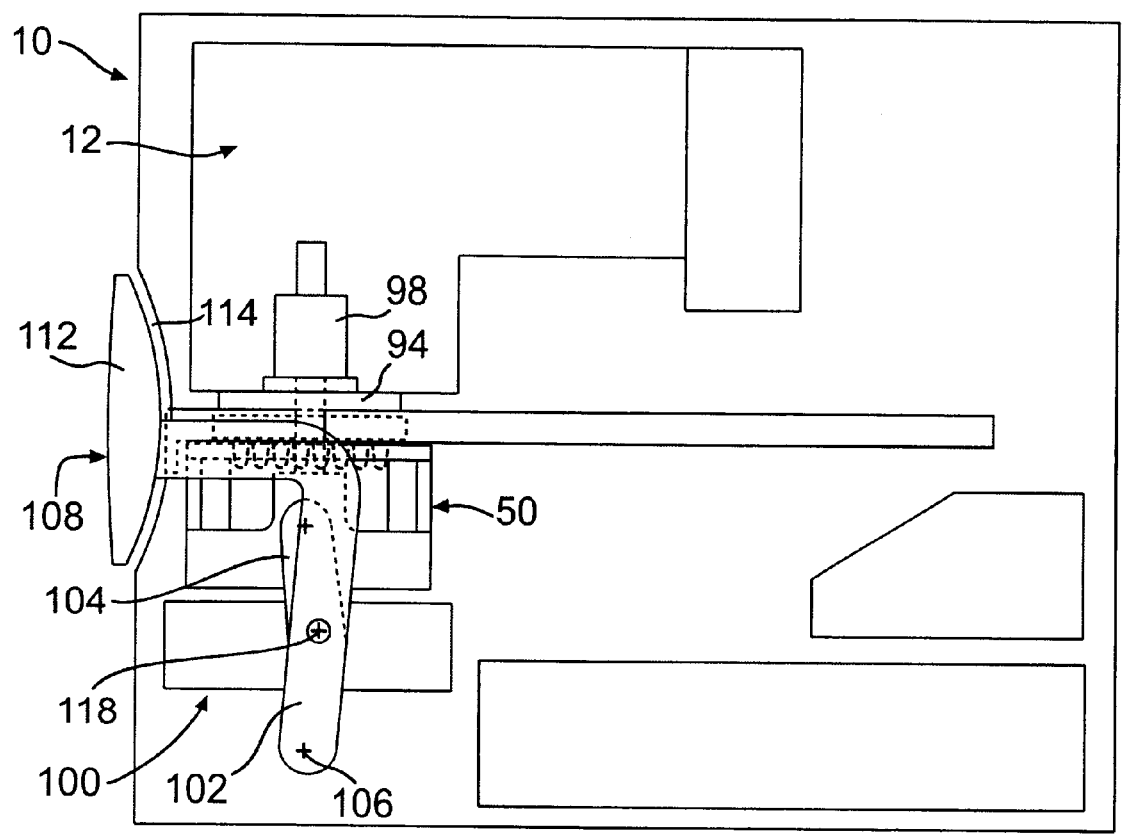
FIG. 3C is a side view of the device of FIG. 3A, with the sample well tray inserted into the device and a sample block assembly in an upward position for engaging the sample well tray.

Further various embodiments of the sample block assembly positioning mechanism contemplate structure such as shown in FIGS. 3A–3C. The positioning mechanism is generally designated by the reference number 100 in FIGS. 3A–3C. The positioning mechanism includes a plurality of links such as first link 102 and second link 104. As shown in FIG. 3A, the first link 102 has a first end rotatably connected to a stationary pivot point 106 and a second end defining a handle 108 for manual manipulation of the first link. In FIGS. 3A–3C, the first link 102 is in the shape of a connecting rod with a bend as shown in FIG. 3A. The handle 108 of the first link 102 defines a door 112 corresponding to an opening 114 in the thermal cycling device. The door 112 is configured to cover the opening 114 in the thermal cycling device when the handle is actuated in a manner described below. Although the door is shown having an arcuate shape on the inner surface, any other suitable shape is also acceptable.

As shown in FIG. 3A, the second link 104 has a first end rotatably connected to a pivot point 118 positioned on first link 102. The second link 104 has a second end rotatably connected to the sample block assembly 50 at pivot point 120. By the linkage arrangement described above, the actuation of the handle 108 will cause the sample block assembly 50 to translate in the vertical direction.

An operation of the thermal cycling device for the embodiment of FIGS. 3A–3C will be briefly described below. To the extent that the following operation is similar to the operation described above for the embodiment shown in FIGS. 1 and 2A–2C, a detailed description of the operation will not be repeated. Moreover, the same reference numbers will be used to refer to the same or like parts as shown in the embodiment of FIGS. 1 and 2A–2C. FIG. 3A shows the sample well tray holder 30 and sample well tray 14 in an outward position. In FIG. 3A, the sample block assembly 50 is in the downward or "first" position. The sample well tray holder 30 is then inserted into the thermal cycling device 10 by translating in the horizontal direction until the sample well tray 14 reaches its proper aligned position (shown in FIG. 3B) between the optical detection system and the sample block assembly.

After the sample well tray 14 reaches its aligned position, an operator may manually press against the handle 108 to rotate the first link 102 about the stationary pivot point 106. In another embodiment, the handle may be rotated robotically. In either case, the clockwise rotation (in reference to FIGS. 3A–3C) of the first link 102 results in the pivot point 118 moving upward, thereby causing the pivot point 120 on the second link 104 to move upward. The upward movement of the second link results in translation of the sample block assembly 50 in an upward vertical direction to an upward or "second" position (shown in FIG. 3C). The positioning mechanism is configured so that the door 112 is fully closed as shown in FIG. 3C when the top surface of the sample block firmly contacts the sample well tray. When the sample block assembly is in the upward position, as shown in FIG. 3C, the thermal cycling device is ready for thermal cycling processes.

At any desired time, e.g., upon completion of the thermal cycling processes, the handle 108 may be rotated counterclockwise, thereby translating the sample block assembly 50 back to the downward position shown in FIG. 3B. The sample well tray holder can then be slid from the thermal cycling device and returned to the position shown in FIG. 3A, and the sample well tray 14 may be removed from the sample well tray holder.

In accordance with still further embodiments of the positioning mechanism, the plurality of links can comprise a first link and a second link. The first link is rotatably connected to a stationary pivot point. The first link has a first end rotatably connected to the second link and a second end comprising a handle for manual manipulation of the first link. The second link has a first end rotatably connected to the first end of the first link and a second end rotatably connected to the sample block assembly.

Figure 4A:
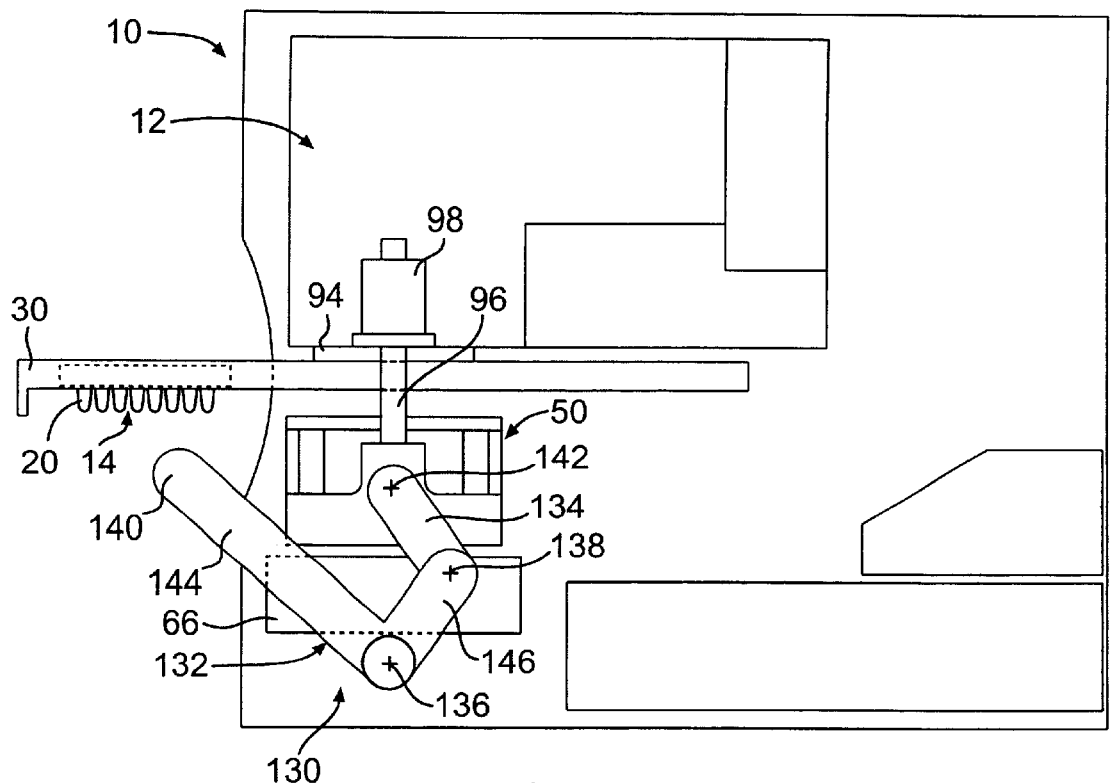
FIG. 4A is side view of yet another embodiment of the thermal cycling device of the invention, with the sample well tray positioned outside of the device.
Figure 4B:
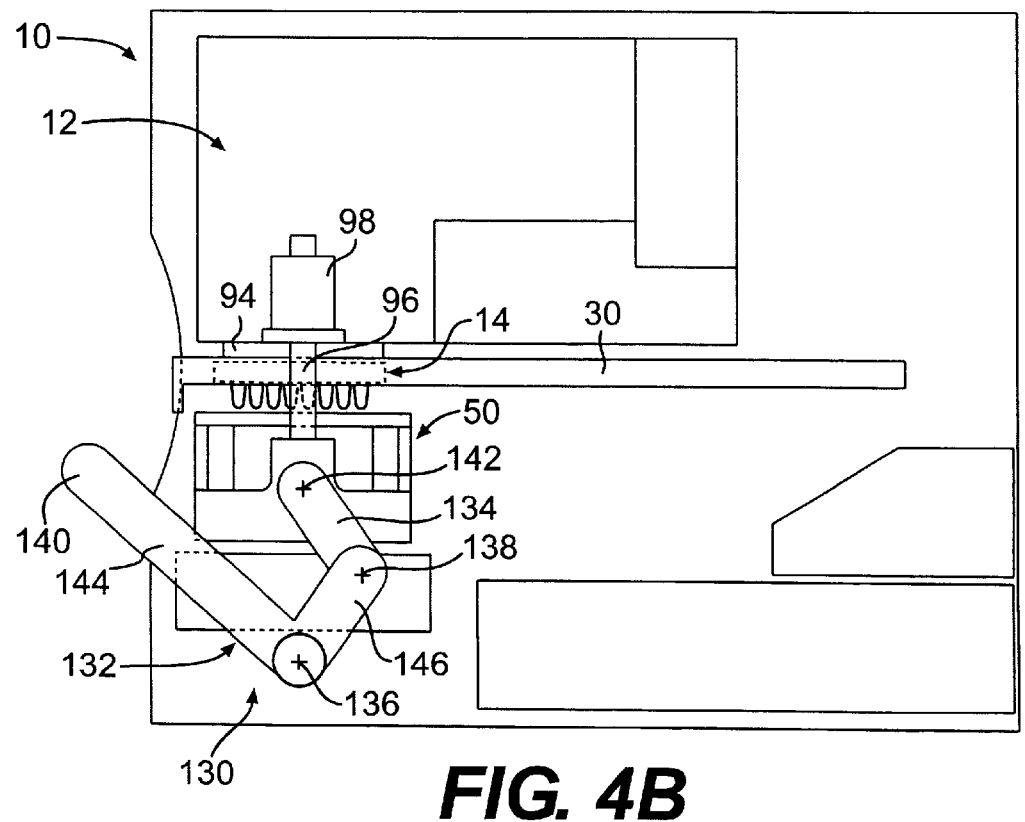
FIG. 4B is a side view of the device of FIG. 4A, with the sample well tray inserted into the device.
Figure 4C:
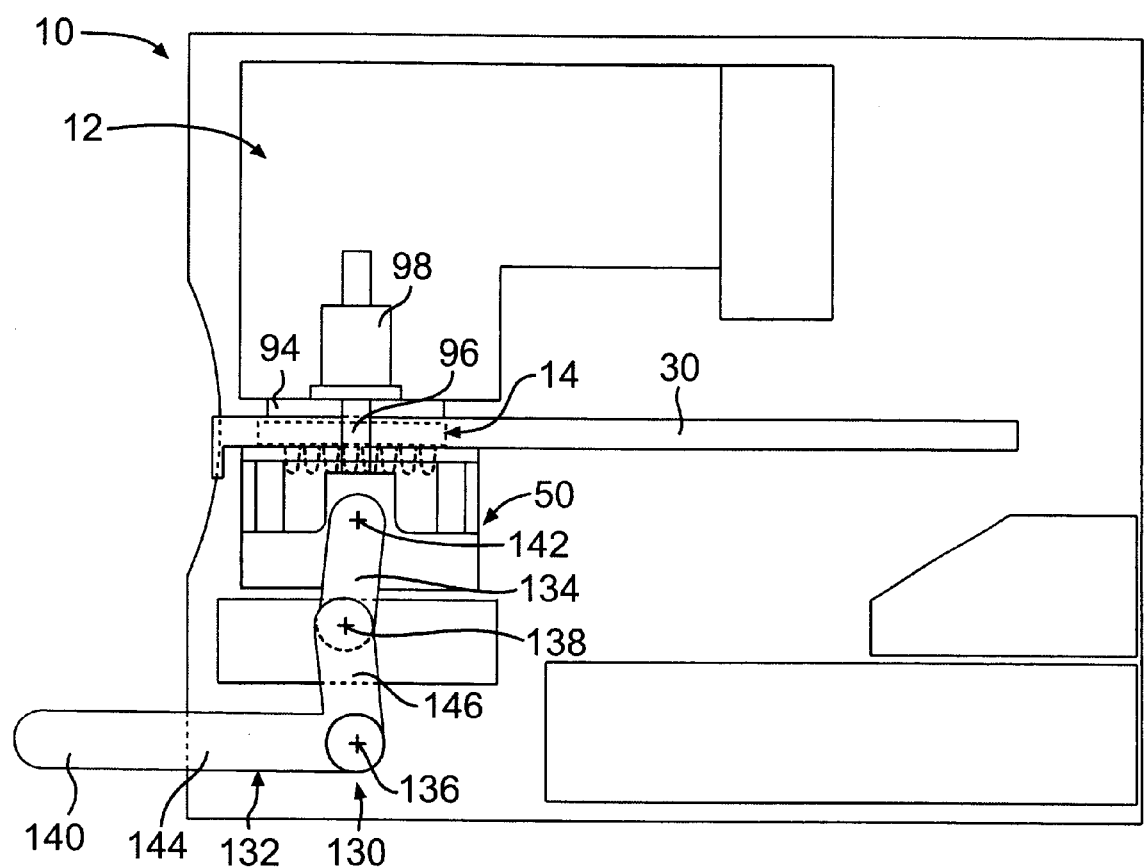
FIG. 4C is a side view of the device of FIG. 4A, with the sample well tray inserted into the device and a sample block assembly in an upward position for engaging the sample well tray.

Such embodiments of the positioning mechanism include that shown in FIGS. 4A–4C. As shown in FIGS. 4A–4C, the positioning mechanism is generally designated by reference number 130. The positioning mechanism 130 includes a plurality of links such as first link 132 and second link 134. As shown in FIGS. 4A–4C, the first link 132 is rotatably connected to a stationary pivot point 136. The first link 132 has a first end rotatably connected to the second link 134 at a pivot point 138. The first link includes a second end comprising a handle 140 for manual or automatic manipulation of the first link 132. The second link 134 includes a first end rotatably connected to the first end of the first link at pivot point 138. The second link 134 further includes a second end rotatably connected to the sample block assembly 50 at pivot point 142.

As shown in FIGS. 4A–4C, the first link 132 includes a first segment 144 and a second segment 146. In FIGS. 4A–4C, the first segment 144 and second segment 146 of the first link are substantially perpendicular to each other. This angle is by way of example only, as the linkages may have various configurations. By the linkage arrangement described above, the actuation of the handle 140 will cause the sample block assembly to translate in the vertical direction.

An operation of the thermal cycling device for the positioning mechanism of FIGS. 4A–4C will be briefly described below. To the extent that the following operation is similar to the operation for the other embodiments described above, a detailed description of the operation will not be repeated. FIG. 4A shows the sample well tray holder 30 and sample well tray 14 in an outward position. In FIG. 4A, the sample block assembly 50 is in the downward or "first" position. The sample well tray holder 30 is then inserted into the thermal cycling device 10 by translating in the horizontal direction until the sample well tray reaches its proper aligned position (shown in FIG. 4B).

After the sample well tray reaches its aligned position, an operator may manually or automatically press downward against the handle 140 to rotate the first link 132 about the stationary pivot point 136 in a counterclockwise direction (in reference to FIGS. 4A–4C). This counterclockwise rotation of the first link 132 results in the pivot point 138 moving upwardly thereby causing the second link 134 to move upwardly. The upward movement of the second link results in translation of the sample block assembly 50 in an upward vertical direction to an upward or "second" position. FIG. 4C shows the sample block assembly in the upward or "second" position. When the sample block assembly is in the upward position, as shown in FIG. 4C, the thermal cycling device is ready for thermal cycling processes.

At any desired time, e.g., upon completion of the thermal cycling processes, the handle 104 may be rotated clockwise, thereby translating the sample block assembly 50 back to the downward position as shown in FIG. 4B. The sample well tray holder 30 can then be slid from the thermal cycling device and returned to the position shown in FIG. 4A, and the sample well tray 14 may be removed from the sample well tray holder.

The sample block assembly positioning mechanisms shown in the figures are provided for purposes of example only. Other positioning mechanisms could be, for example, a hydraulic, a spring, a lever, a cam, a solenoid, or any other suitable motion-producing device.

As is clear from the above description, the present invention includes a method of performing nucleic acid amplification on a plurality of biological samples positioned in a sample well tray in a thermal cycling device. The method includes the step of placing the sample well tray into a sample well tray holder. The sample well tray 14 shown in the figures is configured for placement into a corresponding recess in the sample well tray holder 30.

The method further includes the step of translating the sample well tray holder and sample well tray into the thermal cycling device until the sample well tray is aligned with a sample block assembly positioned beneath the sample well tray. In one aspect, the translation of the sample well tray holder is in the horizontal direction. The aligned position is shown for example in FIG. 2B. The method further includes the step of translating the sample block assembly from a first position to a second position. In one aspect, the translation of the sample block assembly is in the vertical direction. In the first position, the sample block assembly permits the sample well tray to translate into alignment with the sample block assembly. The first position of the sample block assembly 50 is shown for example in FIG. 2B. In the second position, the sample block assembly is positioned vertically upward relative to the first position in order to contact the sample block assembly to the sample well tray. The second position of the sample block assembly 50 is shown for example in FIG. 2C.

The method further comprises thermally cycling the device while simultaneously optically detecting the samples. An optical detection system 12 is positioned within the thermal cycling device 10 for detecting the characteristics of the sample. The method further comprises translating the sample block assembly from the second position to the first position. Finally, the method comprises the step of removing the sample well tray from the thermal cycling device. The optical detection system remains substantially stationary throughout the above steps.

It is clear that the present invention is not limited to the examples shown. For example, a thermal cycling device could be configured to handle several sample well trays, e.g., positioned side by side. Such an arrangement could include a corresponding optical system and sample block.

It will be apparent to those skilled in the art that various modifications and variations can be made to the structure. Thus, it should be understood that the invention is not limited to the examples discussed in the specification. Rather, the present invention is intended to cover modifications and variations.

What is claimed is:

1. A thermal cycling device, comprising:
   a sample block assembly;
   an optical detection system positioned above the sample block assembly; and
   a sample well tray holder including a tray-receiving region configured to hold a sample well tray, the sample well tray holder configured to translate the sample well tray into alignment with the sample block assembly, wherein the sample block assembly is adapted for movement between a first position permitting the translation of the sample well tray into alignment with the sample block assembly, and a second position, upward relative to the first position, where the sample block assembly contacts the sample well tray.

2. The thermal cycling device of claim 1, wherein the optical detection system is adapted to remain substantially stationary during insertion and removal of the sample well tray from the thermal cycling device.

3. The thermal cycling device of claim 1, wherein the sample block assembly comprises a sample block for contacting the sample well tray when the sample block assembly is in the second position.

4. The thermal cycling device of claim 3, further comprising a positioning mechanism configured to translate the sample block between the first and second positions.

5. The thermal cycling device of claim 4, wherein the positioning mechanism comprises a plurality of links.

6. The thermal cycling device of claim 5, wherein the positioning mechanism is configured so that movement of one of the plurality of links causes movement of another of the plurality of links, thereby causing the translation of the sample block assembly between the first and second positions.

7. The thermal cycling device of claim 5, wherein the positioning mechanism further comprises a motor, and further wherein the plurality of links comprises a first link, a second link, and a third link, and further wherein a first end of the first link is rotatably connected to the motor, a second end of the first link is rotatably connected to the first end of both the second link and the third link, the second link having a second end rotatably connected to a stationary pivot point, the third link having a second end rotatably connected to the sample block assembly, and further wherein the motor causes the first link to translate, thereby causing the second end of the third link to translate the sample block assembly between the first and second positions.

8. The thermal cycling device of claim 7, wherein the plurality of links comprises a first set of links and a second set of links, the first and second set of links being positioned on opposite sides of the sample block assembly.

9. The thermal cycling device of claim 5, wherein the plurality of links comprises a first link and a second link, the first link having a first end rotatably connected to a stationary pivot point, the first link having a second end comprising a handle for manipulation of the first link, the second link having a first end rotatably connected to a pivot point on the first link, the second link having a second end rotatably connected to the sample block assembly, wherein the rotation of the first link about the stationary pivot point causes the second link to translate, thereby translating the sample block assembly between the first and second positions.

10. The thermal cycling device of claim 9, wherein the handle of the first link further comprises a door corresponding to an opening in the thermal cycling device, wherein the door covers the opening in the thermal cycling device when the sample block assembly is in the second position.

11. The thermal cycling device of claim 9, wherein the plurality of links comprises a first set of links and a second set of links, the first and second set of links being positioned on opposite sides of the sample block assembly.

12. The thermal cycling device of claim 5, wherein the plurality of links comprises a first link and a second link, the first link being rotatably connected to a stationary pivot point, the first link having a first end rotatably connected to the second link, the first link having a second end comprising a handle for manual manipulation of the first link, the second link having a first end rotatably connected to the first end of the first link, the second link having a second end rotatably connected to the sample block assembly, wherein the rotation of the first link about the stationary pivot point causes the second link to translate, thereby translating the sample block assembly between the first and second positions.

13. The thermal cycling device of claim 12, wherein the plurality of links comprises a first set of links and a second set of links, the first and second set of links being positioned on opposite sides of the sample block assembly.

14. The thermal cycling device of claim 1, wherein the thermal cycling device is configured to perform thermal cycling when the sample well tray is aligned with the sample block assembly and the sample block assembly is positioned in the second position.

15. The thermal cycling device of claim 1, wherein the tray-receiving region of the sample well tray holder comprises a recess in which the sample well tray may be positioned.

16. The thermal cycling device of claim 1, wherein the thermal cycling device is a real-time PCR machine.

17. A method of performing nucleic acid amplification on a plurality of biological samples positioned in a sample well tray in a thermal cycling device, comprising the steps of:

placing the sample well tray onto a tray-receiving region of a sample well tray holder;

translating the sample well tray holder and sample well tray into the thermal cycling device until the sample well tray is aligned with a sample block assembly positioned beneath the sample well tray;

translating the sample block assembly from a first position wherein the sample block assembly permits the sample well tray to translate into alignment with the sample block assembly, to a second position wherein the sample block assembly is positioned vertically upward relative to the first position to contact the sample well tray;

thermally cycling the device while simultaneously optically detecting the samples;

translating the sample block assembly from the second position to the first position; and removing the sample well tray from the thermal cycling device, wherein the optical detection system remains substantially stationary throughout the above steps.

18. The method of performing nucleic acid amplification of claim 17, wherein the steps of translating the sample block assembly include the step of imparting a force on a first link in order to create movement of the first link.

19. The method of performing nucleic acid amplification of claim 18, wherein the movement of the first link imparts a force on a second link to create movement of the second link and the sample block assembly.

20. A thermal cycling device, comprising:

an optical detection system;

a sample block adapted for movement along a first path, toward and away from the optical detection system; and a sample well tray holder including a tray-receiving region, the sample well tray holder being adapted for movement along a second path, toward and away from a position whereat the tray-receiving region is disposed between the optical detection system and the sample block, wherein the optical detection system is adapted to remain substantially stationary during movement of the sample block and the sample well tray holder along the first and second paths.

21. The thermal cycling device of claim 20, wherein the sample block is configured to allow the sample well tray holder to move along the second path when the sample block is in a first position away from the optical detection system.

22. The thermal cycling device of claim 21, wherein the sample block is configured to contact a sample well tray received in the tray-receiving region of the sample well tray holder when the tray-receiving region is disposed between the optical detection system and the sample block, and the sample block is in a second position toward the optical detection system.

23. The thermal cycling device of claim 22, further comprising a positioning mechanism configured to translate the sample block between the first and second positions.

24. The thermal cycling device of claim 23, wherein the positioning mechanism comprises a plurality of links.

25. The thermal cycling device of claim 24, wherein the positioning mechanism is configured so that movement of one of the plurality of links causes movement of another of the plurality of links, thereby causing the translation of the sample block between the first and second positions.

26. The thermal cycling device of claim 24, wherein the positioning mechanism further comprises a motor, and further wherein the plurality of links comprises a first link, a second link, and a third link, and further wherein a first end of the first link is rotatably connected to the motor, a second end of the first link is rotatably connected to the first end of both the second link and the third link, the second link having a second end rotatably connected to a stationary pivot point, the third link having a second end rotatably connected to the sample block, and further wherein the motor causes the first link to translate, thereby causing the second end of the third link to translate the sample block between the first and second positions.

27. The thermal cycling device of claim 26, wherein the plurality of links comprises a first set of links and a second set of links, the first and second set of links being positioned on opposite sides of the sample block.

28. The thermal cycling device of claim 24, wherein the plurality of links comprises a first link and a second link, the first link having a first end rotatably connected to a stationary pivot point, the first link having a second end comprising a handle for manipulation of the first link, the second link having a first end rotatably connected to a pivot point on the first link, the second link having a second end rotatably connected to the sample block, wherein the rotation of the first link about the stationary pivot point causes the second link to translate, thereby translating the sample block between the first and second positions.

29. The thermal cycling device of claim 28, wherein the handle of the first link further comprises a door corresponding to an opening in the thermal cycling device, wherein the door covers the opening in the thermal cycling device when the sample block is in the second position.

30. The thermal cycling device of claim 28, wherein the plurality of links comprises a first set of links and a second set of links, the first and second set of links being positioned on opposite sides of the sample block.

31. The thermal cycling device of claim 24, wherein the plurality of links comprises a first link and a second link, the first link being rotatably connected to a stationary pivot point, the first link having a first end rotatably connected to the second link, the first link having a second end comprising a handle for manual manipulation of the first link, the second link having a first end rotatably connected to the first end of the first link, the second link having a second end rotatably connected to the sample block, wherein the rotation of the first link about the stationary pivot point causes the second link to translate, thereby translating the sample block between the first and second positions.

32. The thermal cycling device of claim 31, wherein the plurality of links comprises a first set of links and a second set of links, the first and second set of links being positioned on opposite sides of the sample block.

33. The thermal cycling device of claim 20, wherein the thermal cycling device is configured to perform thermal cycling when the tray-receiving region of the sample well tray holder is disposed between the optical detection system and the sample block, and the sample block is in a position toward the optical detection system.

34. The thermal cycling device of claim 20, wherein the tray-receiving region of the sample well tray holder comprises a recess in which a sample well tray may be positioned.

35. The thermal cycling device of claim 20, wherein the thermal cycling device is a real-time PCR machine.

* * * * *